United States Patent
Okuzono (10) Patent No.: US 6,739,750 B2
(45) Date of Patent: May 25, 2004

(54) SAMPLING VESSEL FOR THERMAL ANALYSIS OF MOLTEN METAL

(75) Inventor: Tsuyoshi Okuzono, Akune (JP)

(73) Assignee: Yuwa Co., Ltd., Akune (JP)

( * ) Notice: Subject to any disclaimer, the term of this patent is extended or adjusted under 35 U.S.C. 154(b) by 0 days.

(21) Appl. No.: 10/132,759

(22) Filed: Apr. 25, 2002

(65) Prior Publication Data

US 2003/0043883 A1 Mar. 6, 2003

(30) Foreign Application Priority Data

Sep. 4, 2001 (JP) ........................ 2001-267559

(51) Int. Cl.[7] .................. G01K 1/08; G01K 13/00; G01K 1/12
(52) U.S. Cl. .................. 374/157; 374/139; 73/864.61
(58) Field of Search .................. 374/157, 139, 374/140, 179; 73/864.5, 864.6; 136/231, 232, 234, 230; 266/88, 275

(56) References Cited

U.S. PATENT DOCUMENTS

| | | | | |
|---|---|---|---|---|
| 3,267,732 A | * | 8/1966 | Hance | 374/157 |
| 3,844,172 A | * | 10/1974 | Jeric | 374/157 |
| 4,102,197 A | * | 7/1978 | Bardenheuer et al. | 374/157 |
| 4,105,191 A | * | 8/1978 | Charbonnier | 266/275 |
| 4,195,057 A | * | 3/1980 | Patel | 206/525 |
| 4,274,284 A | * | 6/1981 | Hance | 374/157 |
| 4,358,948 A | * | 11/1982 | Plessers | 374/157 |
| 4,570,496 A | * | 2/1986 | Falk | 374/139 |
| 5,037,211 A | * | 8/1991 | Nakashima et al. | 374/139 |
| 5,503,475 A | * | 4/1996 | Yamaguchi | 374/157 |
| 6,106,150 A | * | 8/2000 | Lindholm et al. | 374/139 |
| 6,200,520 B1 | * | 3/2001 | Morinaka et al. | 266/79 |
| 6,271,043 B1 | * | 8/2001 | Godec et al. | 73/864.51 |
| 6,454,459 B1 | * | 9/2002 | Sillién et al. | 374/139 |

FOREIGN PATENT DOCUMENTS

JP    2002257760 A  *  9/2002  .......... G01N/25/00

* cited by examiner

*Primary Examiner*—Diego Gutierrez
*Assistant Examiner*—Mirellys Jagan
(74) *Attorney, Agent, or Firm*—Jordan and Hamburg LLP (57) ABSTRACT

The invention provides a sampling vessel for thermal analysis of molten metal in which the time required for analysis can be shortened and the temperature change rate in eutectic can be reduced as compared with a conventional sampling vessel, so that the eutectic temperature can be obtained easily accurately for a short time. In order to realize the above, the diameter D of a sample chamber 11 is set to be in the range of 16 to 24 mm, the depth L of the sample chamber is set to be 36 mm or more, and the distance LS from an opening 11a of the sample chamber 11 to a temperature sensor 2 is set to be in the range of 7 to 22 mm. Accordingly, the time required for the temperature to reach the eutectic point can be shortened, and the gradient of a cooling curve in eutectic can be reduced.

3 Claims, 9 Drawing Sheets

PRIOR ART

SAMPLING VESSEL FOR THERMAL ANALYSIS OF MOLTEN METAL

BACKGROUND OF THE INVENTION

The present invention relates to a sampling vessel for thermal analysis of molten metal, and more particularly to a sampling vessel for, when a cast material of cast iron, aluminum, an alloy thereof, or the like is to be produced, thermally analyzing the structure of the cast material in front of a furnace.

When cast iron, a light metal such as aluminum, an alloy thereof, or the like is to be cast, the following method is generally adopted for examining the structure of the melt in front of a furnace. The melt is poured into a sampling vessel for thermal analysis provided with a temperature sensor, and a cooling curve of the melt is obtained from an output of the temperature sensor.

As a sampling vessel of this kind, a so-called cup-type vessel is often used. Such a cup-type vessel includes: a vessel body which is made of a heat resisting material, which has a substantially cylindrical bottomed shape, and which comprises a sample chamber having an opening in an upper end; and a temperature sensor such as a thermocouple which is passed through the bottom wall of the sample chamber to be located in the sample chamber. By using a ladle or a dipper, the melt is poured into the sampling vessel from the furnace in which the metal is molten.

Figure 10:
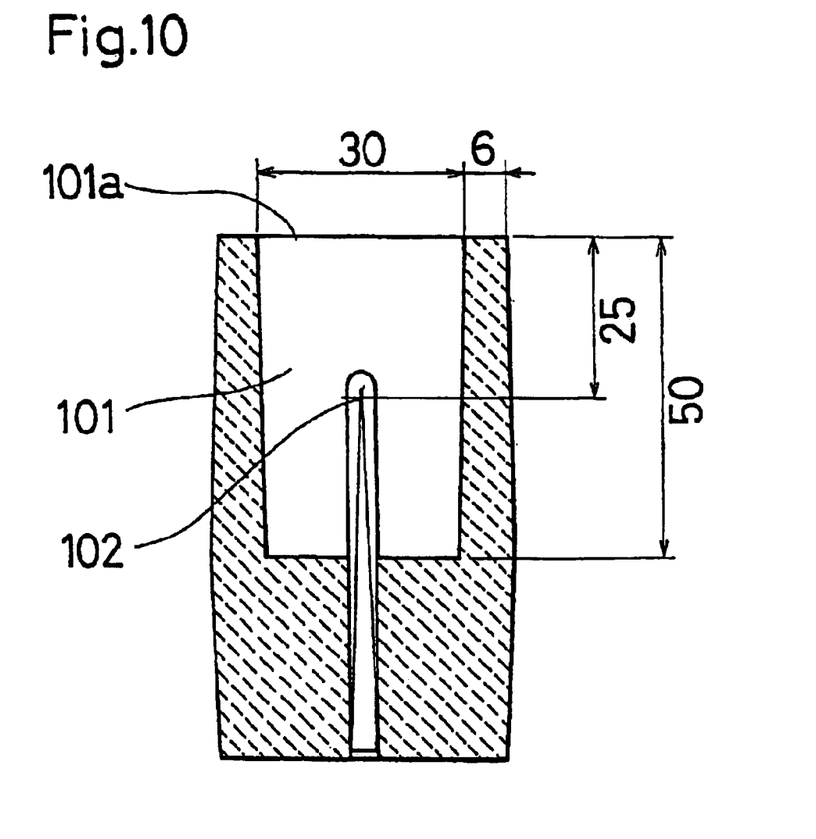
FIG. 10 is a longitudinal section view illustrating a configuration example of a conventional cup-type sampling vessel.

As exemplarily shown in a longitudinal section view of FIG. 10, such a conventional cup-type sampling vessel usually has a sample chamber 101 measuring about 30 mm in diameter and about 50 mm in depth. A temperature sensor 102 is placed in a middle portion in depth of the sample chamber 101, that is, in a position which is separated by about 25 mm from an opening 101a in the upper end of the sample chamber 101.

Another kind of known sampling vessel is a so-called probe-type sampling vessel which is disclosed in Japanese Patent Publication (Kokai) No. 2000-131311. The probe-type sampling vessel comprises: an runner which is adjacent to a sample chamber having an opening in the upper end, the lower end of which is opened, and which communicates with the opening of the sample chamber; an exhaust passage which communicates with the opening of the sample chamber, and the upper end of which is opened in a higher position than the opening of the sample chamber; and a sensor holder which is formed above the sample chamber, and which holds a temperature sensor that is inserted from the opening of the sample chamber into the sample chamber. The sampling vessel has a structure in which these components are integrally formed by a heat resisting material. In the conventional probe-type sampling vessel, the shape and dimensions of the sample chamber are the same as those of the above-described cup-type vessel.

The sampling vessel is produced in the following manner. Two or right and left members respectively having shapes which are formed by dividing the vessel by a dividing plane along the center axis of the sampling vessel, that is, by a dividing plane in the longitudinal direction of the vessel are produced. The members are bonded together in the dividing plane with an adhesive agent.

The probe-type sampling vessel is immersed in the melt, so that the melt is caused to flow into the sample chamber through the runner in which the lower end is opened. In accordance with the flow-in, the air in the interior of the vessel including the sample chamber is exhausted to the outside through the exhaust passage in which the upper end is opened. Accordingly, in the probe-type sampling vessel, the sample chamber can be filled with the melt without using a ladle or a dipper.

In both the above-mentioned conventional cup-type and probe-type sampling vessels, the time required for analysis is relatively long, and the temperature fall rate in eutectic, i.e., the gradient of a cooling curve in eutectic is relatively large. Thus, the vessels involve a problem in that the analytic procedure for determining the eutectic point is complicated.

In the conventional probe-type sampling vessel, the structure is complicated, and the bonding area for the two members is large, thereby producing a problem in that the workability of assembly is poor. Since the two members have a slim shape in which the longitudinal size is larger than the lateral size, each member easily warps during a process of firing the member. Such warping causes a failure to be produced in bonding the two members together. Since the bonding plane exists in a position where the sample chamber is divided into two portions, the adhesive agent may enter in the sample chamber. In this case, the adhesive agent may serve as an impurity to contaminate the melt. For these reasons, it is necessary to provide a large number of inspection steps.

In the conventional probe-type sampling vessel, the exhaust passage is bent in the vessel. When the flow-in melt is cooled, therefore, the metal may obstruct the exhaust passage in the inside thereof, and the gas may not be exhausted. In this case, the sampled melt may be caused by the gas pressure to flow backward or to be diverted, thereby producing the possibility that a predetermined amount of melt cannot be sampled.

Moreover, the conventional probe-type sampling vessel involves an additional problem in that, because of the complication of the inner passage and the large outer dimensions of the whole vessel, a large pushing force is required for immersing the vessel into the melt.

SUMMARY OF THE INVENTION

The invention has been conducted in view of the above-mentioned circumstances. It is a primary object of the invention is to provide a sampling vessel for thermal analysis of molten metal in which the time required for analysis a can be shortened and the temperature change rate in eutectic can be reduced as compared with the conventional cup-type and probe-type sampling vessels, so that the eutectic temperature can be obtained easily accurately for a short time.

It is another object of the invention is to provide a probe-type sampling vessel for thermal analysis of molten metal in which the structure is simple, and the production and inspection steps can be remarkably simplified as compared with the conventional probe-type sampling vessel, and the pushing force required for immersing the vessel into the melt can be reduced.

It is a further object of the invention is to provide a sampling vessel for thermal analysis of molten metal in which there is no possibility that the melt is solidified in the exhaust passage and the air is blocked from being exhausted, as compared with the conventional probe-type sampling vessel.

In order to attain the primary object, the sampling vessel for thermal analysis of molten metal according to the invention is a sampling vessel for thermal analysis of molten metal which is made of a heat resisting material, which has a substantially cylindrical bottomed shape comprising a sample chamber having an opening in an upper end, and in which a temperature sensor is passed through a bottom wall of the sample chamber to be located in the sample chamber, and is characterized in that the sample chamber has a diameter in a range of 16 to 24 mm, and a depth of 36 mm or more, and the temperature sensor is located at a depth in a range of 7 to 22 mm away from the upper-end opening of the sample chamber.

In order to also attain the primary object, the sampling vessel for thermal analysis of molten metal according to the invention is a sampling vessel for thermal analysis of molten metal including: a cylindrical bottomed sample chamber which has an opening in an upper end; a runner which is formed in adjacent to the sample chamber, in which a lower end is opened, and which communicates with the opening of the sample chamber; an exhaust passage which communicates with the opening of the sample chamber, and in which an upper end is opened in a higher position than the opening of the sample chamber; and a sensor holder which is formed above the sample chamber, and which holds a temperature sensor that is inserted into the sample chamber through the opening of the sample chamber, the sample chamber, the runner, the exhaust passage, and the sensor holder being integrally formed by a heat resisting material, and is characterized in that the sample chamber has a diameter in a range of 16 to 24 mm, and a depth of 36 mm or more, and the temperature sensor is located in a position in a range of 7 to 22 mm away from a bottom wall of the sample chamber.

In order to attain the other object, the sampling vessel for thermal analysis of molten metal according to the invention is characterized in that the sampling vessel for thermal analysis of molten metal is configured by two or upper and lower members respectively having shapes which are formed by dividing the vessel by a dividing plane that perpendicularly crosses a center axis of the vessel in a position which is above the sample chamber and not in the sample chamber, and the members are bonded together in the dividing plane.

In order to attain the further object, the sampling vessel for thermal analysis of molten metal is characterized in that the runner and the exhaust passage communicate with each other on a straight line.

In the invention of each of the above-mentioned claims, preferably, a circumference wall of the sample chamber has a thickness of 5.5 mm or more.

The invention has been conducted by eagerly studying the shapes and dimensions of portions of a sampling vessel for thermal analysis of molten metal, so as to optimize them. According to experiments, the diameter of the sample chamber is preferably set to be in the range of 16 to 24 mm, and more preferably in the range of 18 to 21 mm. When the diameter of the sample chamber is smaller than 16 mm, the temperature fall rate in eutectic is large, so that it is difficult to determine the eutectic temperature. When the diameter exceeds 24 mm, the time required for analysis is disadvantageously prolonged, and hence such a large diameter is not preferable.

The depth of the sample chamber is preferably set to be 36 mm or more, and more preferably 40 mm or more. When the depth is less than 36 mm, the temperature fall rate in eutectic is large, so that it is difficult to determine the eutectic temperature.

Moreover, the distance from the upper-end opening of the sample chamber to the temperature sensor in a cup-type sampling vessel, and that from the bottom wall of the sample chamber to the temperature sensor in a probe-type sampling vessel are preferably set to be in the range of 7 to 22 mm, and more preferably in the range of 9 to 17 mm. When the distance from the upper-end opening of the sample chamber to the temperature sensor in the cup-type sampling vessel, or the distance from the bottom wall of the sample chamber to the temperature sensor of the probe-type sampling vessel is less than 7 mm, the melt in the position where the temperature sensor is disposed is easily cooled, so that it is impossible to obtain a good cooling curve. When the distance exceeds 22 mm, the temperature fall rate in eutectic is large, so that it is difficult to determine the eutectic temperature.

With respect to other dimensions of the sample chamber, the thickness of the circumference wall is preferably set to be 5.5 mm or more, and more preferably 6 mm or more. When the thickness is less than 5.5 mm, the temperature fall rate is large, and the time required for analysis is prolonged.

The above-mentioned shapes and dimensions of the various portions of the sample chamber are common to the cup-type sampling vessel and the probe-type sampling vessel. When the configurations of the inventions are adopted, the eutectic temperature can be easily accurately known for a short analysis time.

The sample chamber having the above-mentioned shape and dimensions has smaller outer dimensions as compared with a conventional sample chamber. When the sample chamber is applied to a probe-type sampling vessel, therefore, the dimensions as a whole can be miniaturized as compared with the conventional one, and it is possible to attain reduction of the pushing force which is required for immersing the vessel into the melt.

With respect to the probe-type sampling vessel, when a configuration is employed in which the sampling vessel consisting of the sample chamber, the runner, the exhaust passage, and the sensor holder is configured by two or upper and lower members respectively having shapes which are formed by dividing the vessel by a dividing plane that perpendicularly crosses the center axis of the vessel in a position which is above the sample chamber and not in the sample chamber, and the members are bonded together in the dividing plane, the sampling vessel can attain the following advantages as compared with a conventional probe-type sampling vessel which is divided by a dividing plane along the center axis of the conventional vessel, i.e., divided into a right and a left members. Since the bonding area is reduced, the bonding operation can be simplified. The occurrence of warping in a process of firing each member can be avoided because of the reduced aspect ratio of each member. Since the bonding plane does not cross the sample chamber, the possibility that the adhesive agent may enter the sample chamber can be eliminated. Therefore, the production and inspection steps can be simplified.

Moreover, when a configuration is employed in which the runner and the exhaust passage communicate with each other on a straight line, the internal structure of the probe-type sampling vessel is simplified, and the melt can smoothly flow. Thus, it is possible to suppress the cooling of the melt in the runner. The smooth flow of the melt due to the simplified internal structure of the probe-type sampling vessel contributes together with the above-mentioned reduced outer dimensions to reduction of the pushing force in the process of immersing the vessel into the melt.

BRIEF DESCRIPTION OF THE DRAWINGS

FIG. 1 is an explanatory view of an embodiment in which the invention is applied to a cup-type sampling vessel.

FIG. 3 is a view illustrating influence of a temperature sensor obtained by the above-mentioned experiments.

FIG. 4 is a view illustrating influence of the depth of the sample chamber also obtained by the above-mentioned experiments.

FIG. 5 is a view illustrating influence of the diameter of the sample chamber also obtained by the abovementioned experiments.

FIG. 6 is a view illustrating influence of the circumference wall of the sample chamber also obtained by the above-mentioned experiments.

DETAILED DESCRIPTION OF THE PREFERRED EMBODIMENTS

Hereinafter, preferred embodiments of the invention will be described with reference to the accompanying drawings.

Figure 1A:
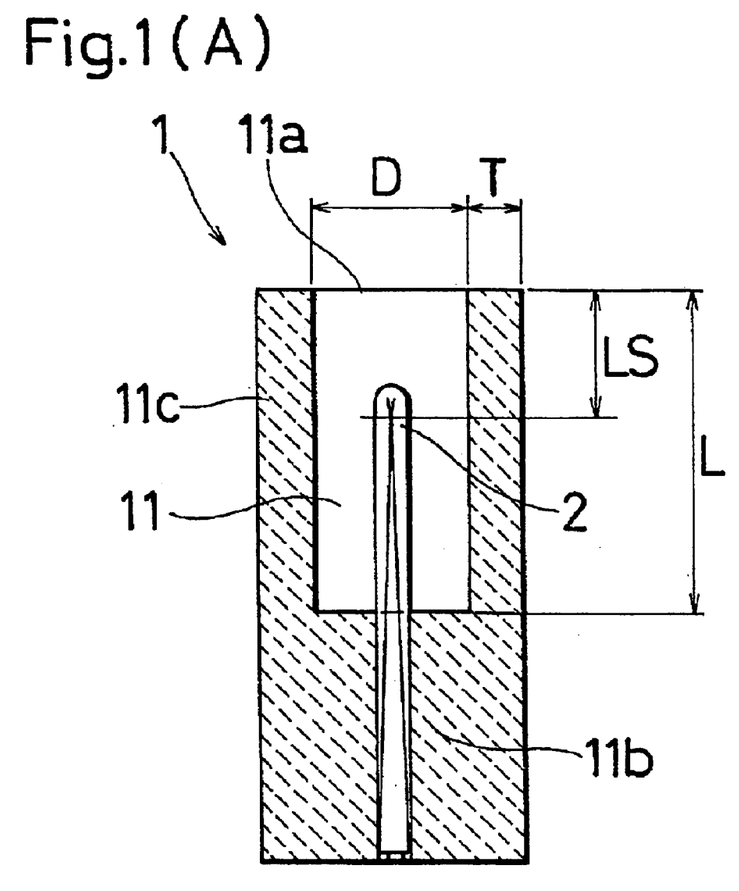
FIG. 1(A) is a longitudinal section view.
Figure 1B:
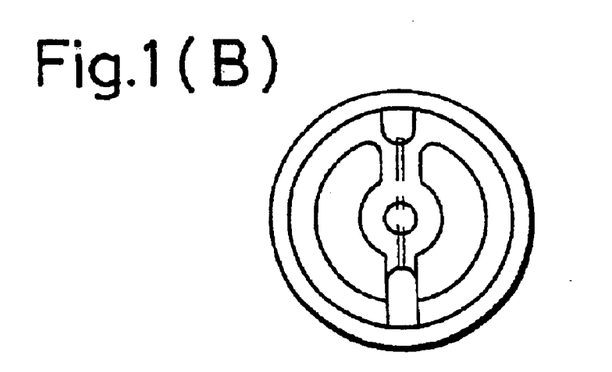
FIG. 1(B) is a bottom view.

FIG. 1 is an explanatory view of an embodiment in which the invention is applied to a cup-type sampling vessel. In FIG. 1, (A) is a longitudinal section view, and (B) is a bottom view.

A sampling vessel 1 is formed by firing a heat resisting material such as ceramics. The sampling vessel 1 has a cup-like shape as a whole, and includes a sample chamber 11 which comprises an opening 11a for pouring a molten metal, in the upper end. A temperature sensor 2 configured by, for example, a thermocouple using a chromel-alumel wire is fixed in a condition where the temperature sensor 2 is inserted into the sample chamber 11 through a bottom wall 11b of the chamber.

In this example, the diameter D of the sample chamber 11 is 20 mm, and the depth L of the chamber is 41 mm. The position of the temperature sensor 2 in the sample chamber 11 is separated by a distance LS of 16 mm from the upper-end opening 11a, and located substantially in the middle in a radial direction of the sample chamber 11.

The thickness T of the circumference wall 11c of the sample chamber 11 is 7 mm. The thickness of the bottom wall 11b is larger than that of the circumference wall 11c, so that the metal melt in the sample chamber 11 is hardly cooled through the bottom wall 11b.

In the above-described embodiment, in the same manner as a conventional cup-type sampling vessel of this kind, a melt of cast iron, aluminum, or an alloy thereof is poured into the vessel with using a dipper, a ladle, or the like through the upper-end opening 11a. The composition of the metal is analyzed from a cooling curve which is obtained by using the output of the temperature sensor 2. According to the embodiment of the invention having the abovementioned dimensions and shapes, it is possible to greatly shorten the time required for analysis as compared with the above-mentioned conventional cup-type sampling vessel of this type, as apparent from the results of the experiments shown below. In addition, the gradient of the cooling curve in eutectic is reduced, so that it is possible to easily determine the eutectic point.

Next, experiments which were performed for the purpose of ascertaining the advantages of the sampling vessel 1 of the embodiment according to the invention will be described. In the experiments, the dimensions of the portions of the cup-type sampling vessel were independently varied, and the influences of the dimensions were studied.

A method for the experiments will be described. Commercially available FCD pig iron of 5.0 kg was molten at 1723K in a graphite crucible placed in a high frequency induction furnace. The temperature was kept for about 30 minutes, so as to produce a hypo-eutectic melt. The melt was poured into the sampling vessel produced for evaluation with using a dipper which was previously sufficiently heated, and then thermal analysis was performed. Based on the obtained cooling curve, the pro-eutectic temperature, the eutectic temperature, and the time required for analysis were measured. In order to determine the shape of the curve, the temperature fall rate in eutectic was calculated.

To the bottom face of the sample chamber of the employed sampling vessel, granular tellurium of 0.3 mass % was bonded by means of zirco-molding so as to realize white pig iron eutectic solidification. Consideration was given to the pouring temperature so as to be kept substantially constant, by pouring the melt at the same time when an $SiO_2$ film began to be formed in the surface of the melt in the dipper.

With respect to the dimensions of the portions of the sampling vessel, the dimensions which were adopted in the above-mentioned embodiment were used as references, and one of the dimensions was independently varied. The materials constituting the sampling vessel were the same in all of the vessels. Specifically, shell sand of 60 mesh was fired at a filling pressure of 1.0 kg/cm$^2$.

Figure 2:
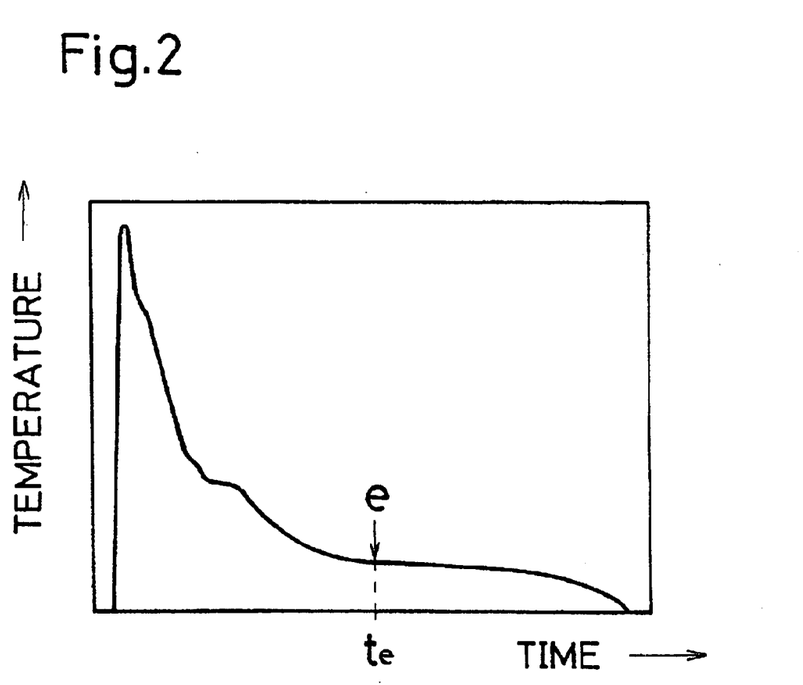
FIG. 2 is a view illustrating an evaluation method in experiments which were performed for evaluating the shape and dimensions of a sample chamber in the invention by using an example of a cooling curve.

The evaluation was performed in the following manner by using the temperature fall rate in eutectic indicated by e in a cooling curve exemplarily shown in FIG. 2, and the time required for analysis which elapsed until the eutectic point indicated by $t_e$ similarly shown in the figure appeared. The temperature fall rate is more preferable, as the rate is closer to 0. When the rate becomes large, the gradient of the cooling curve is increased. Thus, the analytic procedure for determining the eutectic point is complicated, and the measurement accuracy is degraded. In order to shorten the analytic time, preferably, the time required for analysis is as short as possible. Even though the time required for analysis is short, however, it is not preferred that the temperature fall rate is large.

In summary, a sampling vessel in which the temperature fall rate is closer to 0 and the time required for analysis is shorter is evaluated to have a better performance. Results of the experiments will be shown below.

(1) Influence of the sensor position

Figure 3A:
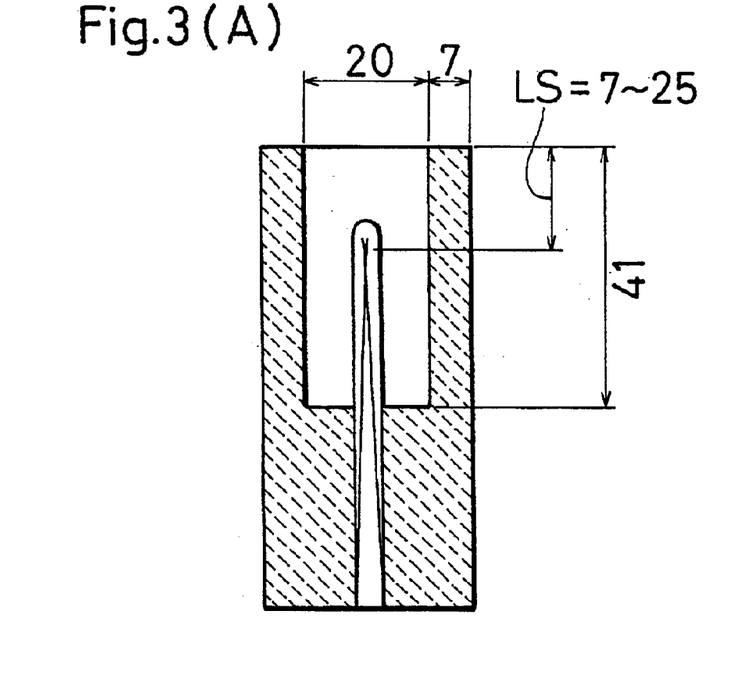
FIG. 3(A) is a view illustrating dimensions of a sampling vessel used in the experiments.

As shown in FIG. 3(A), only the distance LS from the opening of the sample chamber to the temperature sensor was varied, and the other dimensions were fixed to those adopted in the above-mentioned embodiment. In this condition, the temperature fall rate and the time required for analysis were measured. The results are shown in the form of a graph in FIG. 3(B).

Figure 3B:
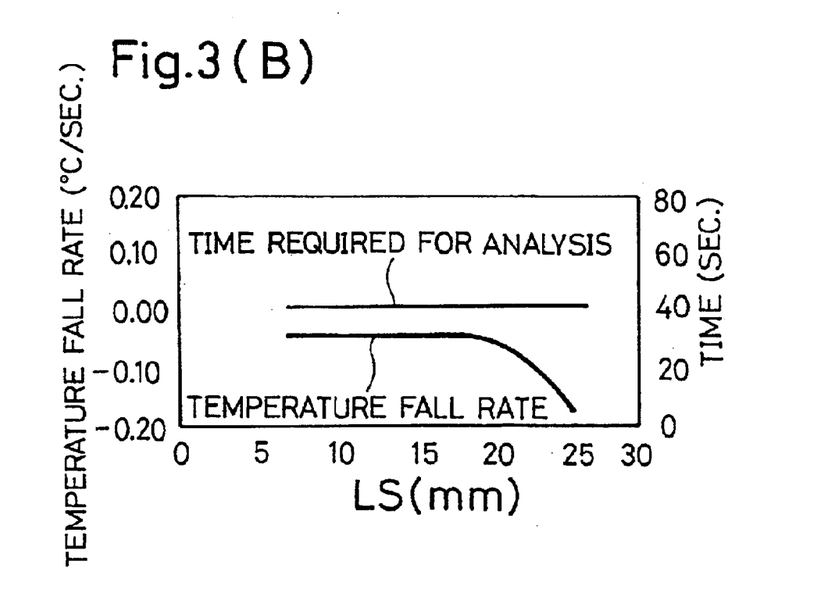
FIG. 3(B) is a graph showing results of the experiments.

It has been found that, as apparent from the graph, the distance LS from the opening of the sample chamber to the temperature sensor does not largely affect the time required for analysis, and, when the distance LS exceeds 17 mm, the temperature fall rate gradually increases. When the distance LS exceeds 22 mm, it is difficult to determine the eutectic point. Although not being considered in this experiment, when the distance LS is less than 7 mm, the cooling curve sufficient for the analysis cannot be obtained.

(2) Influence of the depth of the sample chamber

Figure 4A:
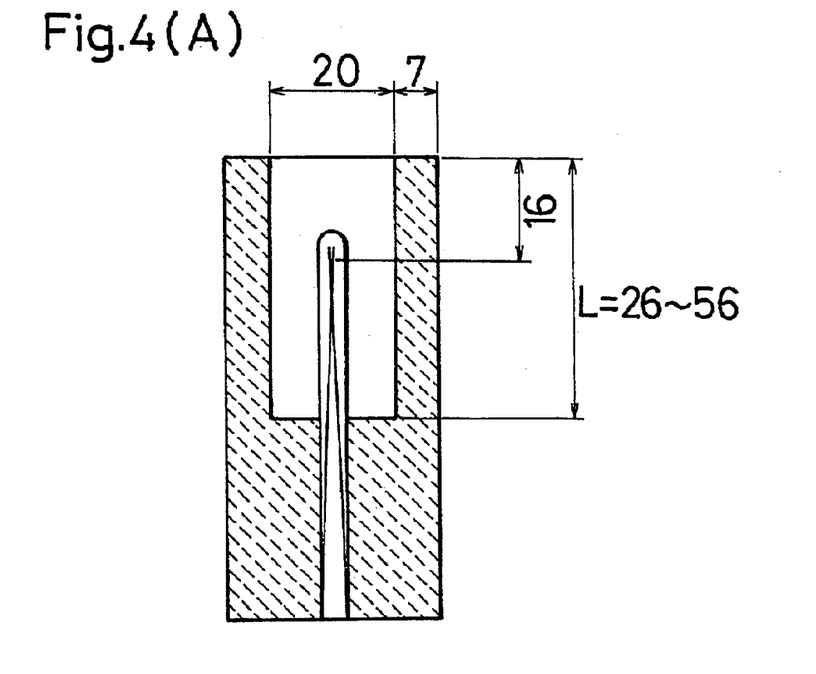
FIG. 4(A) is a view illustrating dimensions of the sampling vessel used in the experiments.

As shown in FIG. 4(A), only the depth L of the sample chamber was varied, and the other dimensions including the distance from the opening of the sample chamber to the temperature sensor were fixed to those adopted in the above-mentioned embodiment. In this condition, the temperature fall rate and the time required for analysis were measured. The results are shown in the form of a graph in FIG. 4(B).

Figure 4B:
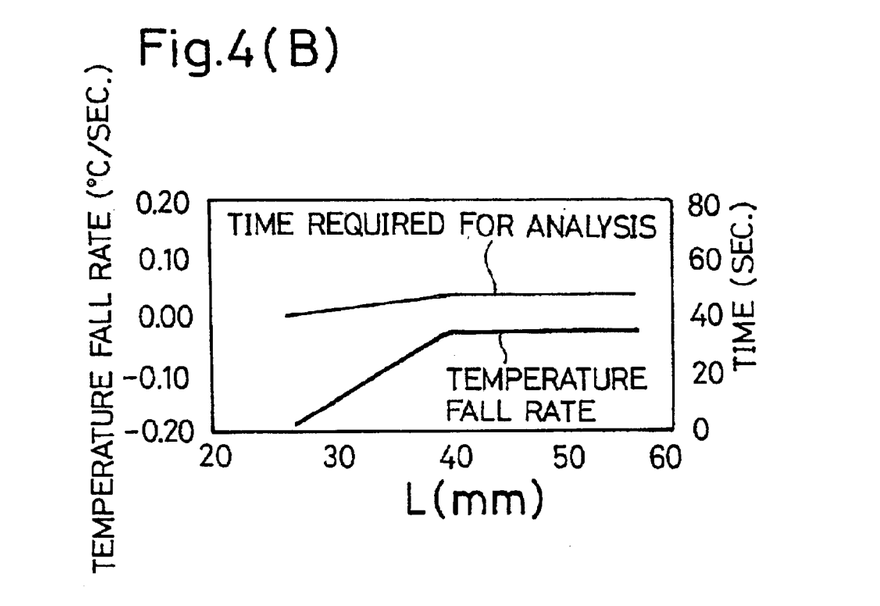
FIG. 4(B) is a graph illustrating results of the experiments.

It has been found that, as shown in the graph, when the depth L of the sample chamber is 40 mm or more, the time required for analysis hardly varies, and, when the depth L is less than 40 mm, the time required for analysis gradually shortens, and signs of improving are shown. The time required for analysis in the case where the depth L is less than 36 mm is shorter by about 5 seconds than that in the case where the depth L is 40 mm or more. The temperature fall rate is substantially constant for the depth L of 40 mm or more, and proportionally increases for the depth L of less than 40 mm. When the depth L is less than 36 mm, it is difficult to determine the eutectic point.

(3) Influence of the diameter of the sample chamber

Figure 5A:
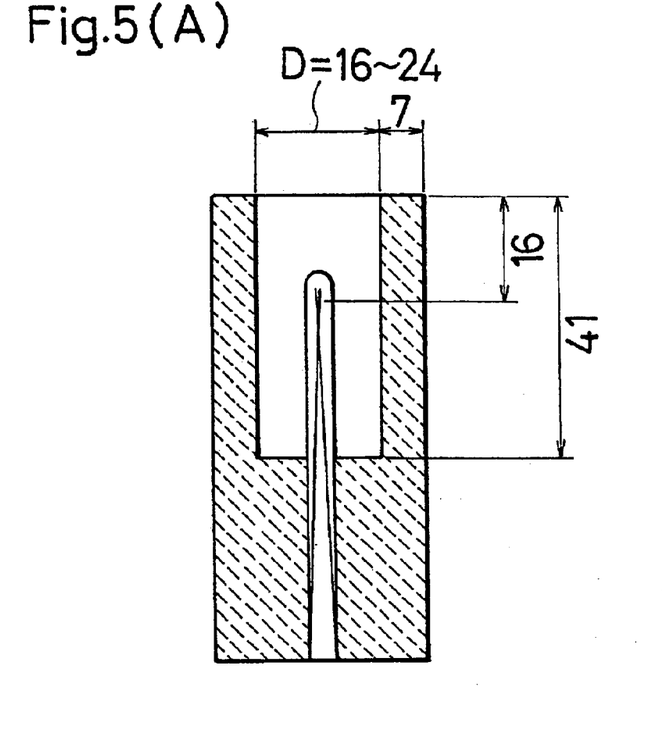
FIG. 5(A) is a view illustrating dimensions of the sampling vessel used in the experiments.
Figure 5B:
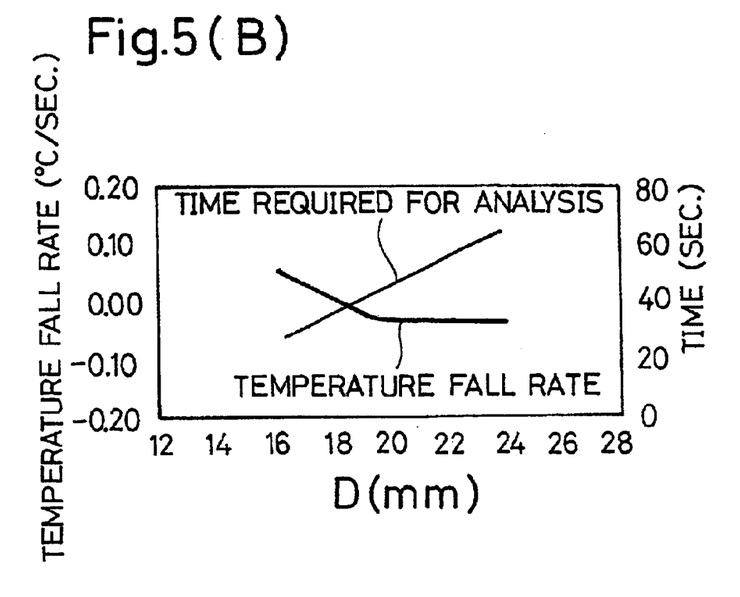
FIG. 5(B) is a graph illustrating results of the experiments.

As shown in FIG. 5(A), only the diameter D of the sample chamber was varied, and the other dimensions were fixed to those adopted in the above-mentioned embodiment. In this condition, the temperature fall rate and the time required for analysis were measured. The results are shown in FIG. 5(B).

As apparent from the graph, the followings were found. When the diameter D of the sample chamber is increased, the time required for analysis lengthens in proportion to the diameter D of the sample chamber. When the diameter D of the sample chamber is 20 mm or more, the temperature fall rate is substantially constant, and, when the diameter D is decreased from the value, the sign of the temperature fall rate is inverted, and the rate gradually increases. When the diameter D is less than 16 mm, it is difficult to determine the eutectic point.

(4) Influence of the thickness of the circumference wall of the sample chamber

Figure 6A:
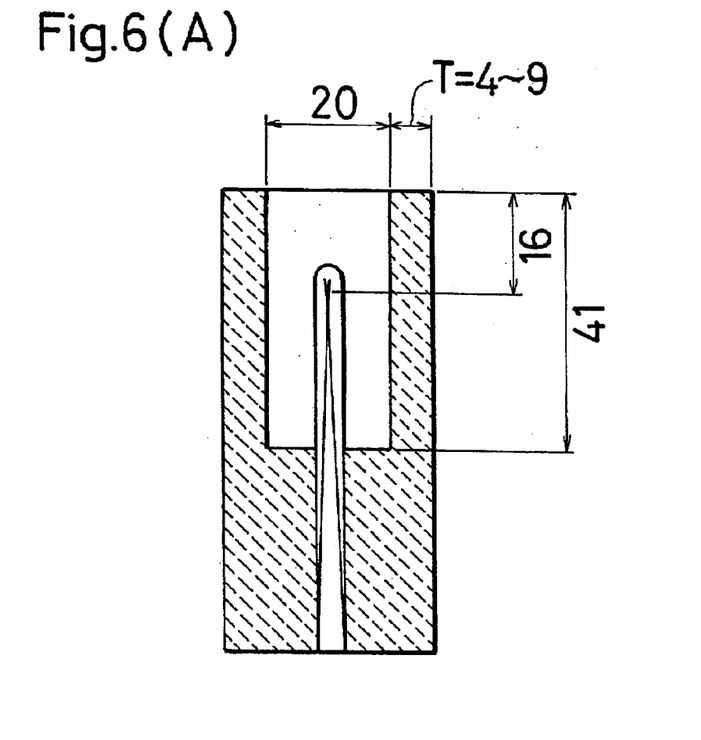
FIG. 6(A) is a view illustrating dimensions of the sampling vessel used in the experiments.
Figure 6B:
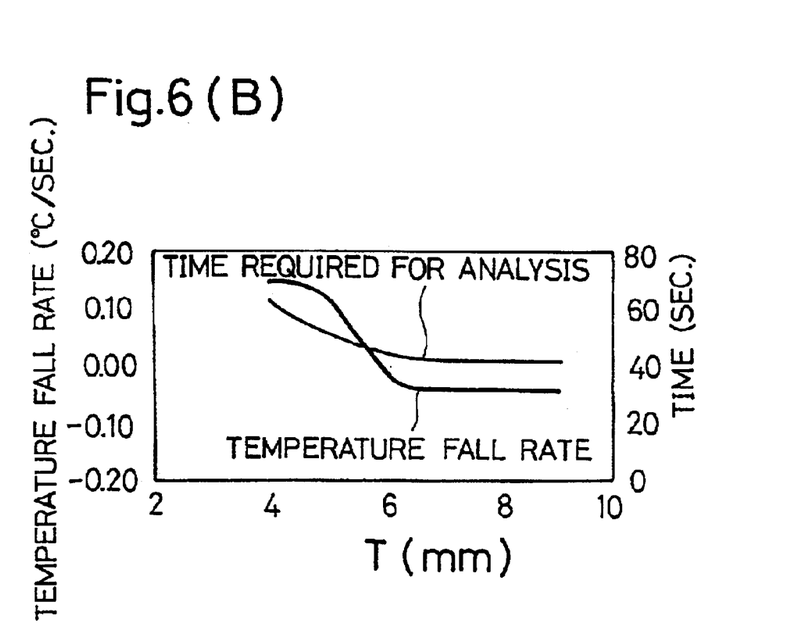
FIG. 6(B) is a graph illustrating results of the experiments.

As shown in FIG. 6(A), only the thickness T of the circumference wall of the sample chamber was varied, and the other dimensions were fixed to those adopted in the above-mentioned embodiment. In this condition, the temperature fall rate and the time required for analysis were measured. The results are shown in FIG. 6(B).

As shown in the graph, when the thickness T of the circumference wall of the sample chamber is 6 mm or more, the time required for analysis is substantially constant, and, when the thickness T is less than 6 mm, the time required for analysis gradually lengthens. It has been found that, when the thickness T is 7 mm or more, the temperature fall rate is substantially constant, when the thickness T is less than 6 mm, the sign is reversed so that the temperature fall rate gradually increases, and, when the thickness T is less than 5.5 mm, it is difficult to determine the eutectic point.

With respect to the sampling vessel 1 in the embodiment of the invention, i.e., the sampling vessel 1 having the shapes and dimensions which were adopted as the references in the above-mentioned experiments, and the conventional cup-type sampling vessel shown in FIG. 10, the time required for analysis and the temperature fall rate were measured in the same way as described above. As a result, the time required for analysis in the conventional vessel was 104 seconds. By contrast, the time required for analysis in the embodiment of the invention was 44 seconds or shortened to one half or less of the time in the conventional one. The temperature fall rate in the conventional one was 0.05° C./sec., but the temperature fall rate in the embodiment of the invention was 0.04° C./sec. which was improved by about 20%.

Next, an embodiment in which the invention is applied to a probe-type sampling vessel will be described.

Figure 7:
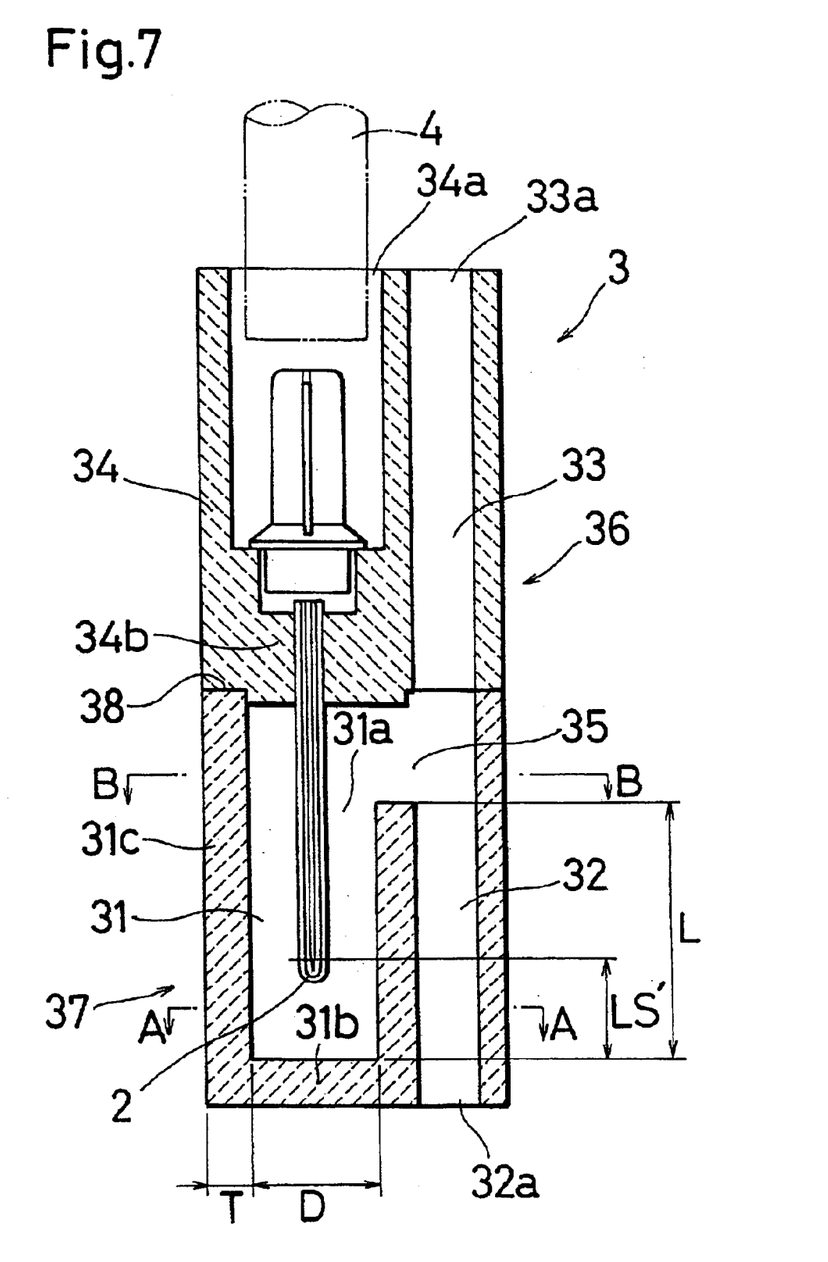
FIG. 7 is a longitudinal section view of an embodiment in which the invention is applied to a probe-type sampling vessel.
Figure 8:
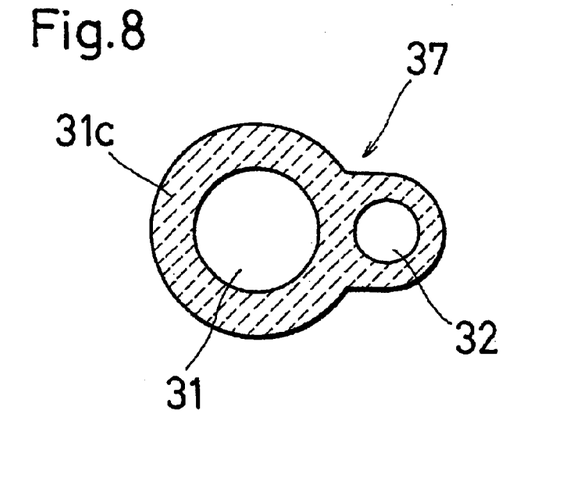
FIG. 8 is a section view taken along the line A—A of FIG. 7.
Figure 9:
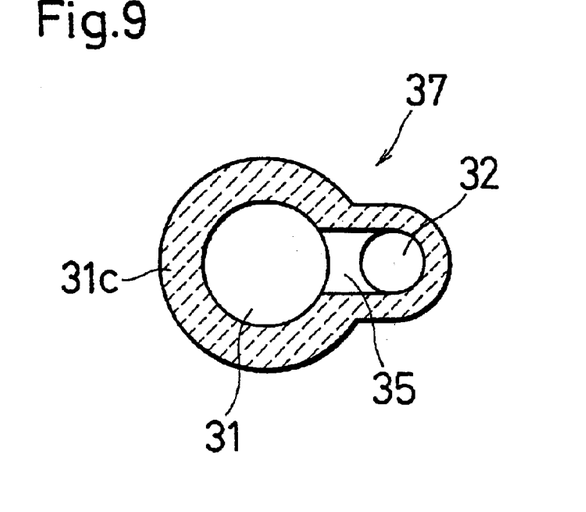
FIG. 9 is a section view taken along the line B—B of FIG. 7.

FIG. 7 is a longitudinal section view of the embodiment, FIG. 8 is a section view taken along the line A—A of FIG. 7, and FIG. 9 is a section view taken along the line B—B of the figure.

In the same manner as the embodiment described above, a sampling vessel 3 in the embodiment is formed by a heat resisting material such as ceramics. The sampling vessel 3 includes a cup-like sample chamber 31, a runner 32, an exhaust passage 33, and a sensor holder 34 which are integrally formed. The sample chamber 31 has an opening 31a in an upper end portion, and is provided with a bottom wall 31b. The runner 32 includes an opening 32a in the lower end, and communicates with the opening 31a of the sample chamber 31. The exhaust passage 33 also communicates with the opening 31a of the sample chamber 31, and is provided with an opening 33a which is opened in the upper end and in a higher position than the opening 31a of the sample chamber 31. The sensor holder 34 is positioned above the sample chamber 31 and holds a temperature sensor 2 which is inserted into the sample chamber 31 through the opening 31a of the sample chamber 31.

The runner 32 is formed in parallel with the center axis of the sample chamber 31 and adjacently to the sample chamber 31. The exhaust passage 33 is formed on an extension line directly above the runner 32. In other words, the runner 32 and the exhaust passage 33 are positioned on a straight line, and communicate with each other. Thus, the runner 32 and the exhaust passage 33 are actually constituted by a linear longitudinal through hole having the openings 32a and 33a in the lower and upper ends of the sampling vessel 3, respectively, and have a structure in which a middle portion of the longitudinal through hole communicates with the opening 31a of the sample chamber 31 through a lateral hole 35.

The sensor holder 34 is formed directly above the sample chamber 31. An opening 34a is formed in the upper end of the holder. The holder has a bottom wall 34b. A temperature sensor 2 is fixed in a condition where the temperature sensor is inserted into the sample chamber 31 through the bottom wall 34b. The temperature sensor 2 is configured by a thermocouple or the like which is similar to that used in the above-mentioned embodiment.

The sampling vessel 3 which is structured as described above is configured by bonding an upper member 36 and a lower member 37 with an adhesive agent or the like. In the upper member 36, the exhaust passage 33 and the sensor holder 34 are formed. In the lower member 37, the sample chamber 31, the runner 32, and the lateral hole 33 are formed. A bonding plane of these members does not cross the sample chamber 31, but is positioned above the sample chamber 31, and perpendicular to the center axis of the sampling vessel 3.

In the embodiment, the diameter D of the sample chamber 31 is 20 mm, and the depth L thereof is 41 mm. The position of the temperature sensor 2 in the sample chamber 31 is separated by a distance LS' of 16 mm from the bottom wall 31b, and located substantially in the middle in a radial direction of the sample chamber 31. The thickness of the circumference wall 31c of the sample chamber 31 is 7 mm, and also the thickness of the base wall 31b is 7 mm.

In the above-described embodiment, in the same manner as a conventional prove-type sampling vessel of this kind, a rod 4 configured by a cardboard tube or the like is inserted into the upper-end opening 34a of the sensor holder 34, and the sampling vessel 3 is then immersed in the melt. Thus, the melt enters through the lower-end opening 32a of the runner 32, and flows into the sample chamber 31 via the runner 32 and the lateral hole 35. During this process, the air in the runner 32 and the sample chamber 31 is exhausted to the outside from the upper-end opening 33a through the exhaust passage 33 in accordance with the entrance of the melt.

The dimensions of the sample chamber 31 in the embodiment are the same as those of the sample chamber 11 in the previous embodiment except that the position of the temperature sensor 2 is separated by 7 mm from the bottom wall 31b of the sample chamber 31 in contrast that the position of the temperature sensor 2 in the previous embodiment is separated by 7 mm from the opening 11a of the sample chamber 11. This configuration is employed because of the following phenomenon. In the probe-type sampling vessel 3, the sensor holder 34 exists above the upper-end opening 31a of the sample chamber 31, and the temperature reduction of the melt through the opening 31a is relatively small. As compared with the bottom wall 11b of the sample chamber 11 in the cup-type sampling vessel 1 in the previous embodiment, the thin bottom wall 31b is employed in the probe-type sampling vessel 3, and hence the melt is easily cooled through the bottom wall 31b. It has been confirmed by experiments that the distance LS' between the temperature sensor 2 and the bottom wall 31b exerts the same influence on the temperature fall rate in eutectic as the distance LS in the previous embodiment.

With the adoption of the sample chamber 31 having such a shape and dimensions, as compared with the above-mentioned conventional probe-type sampling vessel of this kind, the time required for analysis can be greatly shortened. In addition, since the gradient of the cooling curve in eutectic is small, the eutectic point can be easily determined.

Moreover, in this probe-type embodiment, the sample chamber 31 is smaller than the conventional one, it is therefore possible to reduce the outer diameter of the sampling vessel 3 as a whole, with the result that it is possible to reduce the pushing force which is required for immersing the vessel into the melt.

In addition, the sampling vessel 3 is divided by the dividing plane that perpendicularly crosses the center axis of the vessel 3 in a position which is above the sample chamber and not in the sample chamber, and the upper member 36 and the lower member 37 are bonded together in the dividing plane. As compared with the conventional probe-type sampling vessel in which the right and left members separated by a dividing plane along the center axis of the vessel are bonded together in the dividing plane, therefore, the bonding area is reduced, and the bonding operation is easily performed. Moreover, the aspect ratios of the upper and lower members 36 and 37 are smaller than those of the two members in the conventional art which are laterally separated from each other. Accordingly, it is advantageous that any warping cannot occur in a process of firing respective members. In the embodiment of the invention, since the bonding plane 38 between the upper member 36 and the lower member 37 does not cross the sample chamber 31, i.e., since the melt entering the sample chamber 31 does not come into contact with the bonding plane 38, there is no fear that the adhesive agent for bonding is contaminated with the melt. For the above-mentioned reasons, according to the embodiment, the production and inspection steps can be remarkably simplified as compared with the conventional probe-type sampling vessel.

In addition, the above-described embodiment adopts the simple internal structure in which the runner 32 and the exhaust passage 33 communicate with each other on a straight line. Thus, the melt smoothly flows, and it is possible to suppress the cooling of the melt before reaching the sample chamber 31. The smooth flow of the melt contributes together with the above-mentioned reduced outer dimensions to the reduction in the pushing force required for immersing the vessel into the melt.

In the above-described embodiments of the cup-type and probe-type vessels, only one sample chamber 11 or 31 is provided. It is a matter of course that the invention can be equally applied to a known multi-cup type or multi-probe type vessel in which the same sample chambers 11 or 31 are arranged side by side and integrated with one another.

In the above-described embodiment of the cup-type vessel, in order to easily pour the melt, a cylindrical member having a diameter which is larger than that of the sample chamber 11 may be integrally formed above the opening 11a of the sample chamber 11 so as to play the role of a funnel.

As described above, according to the invention, in both the cup-type and probe-type sampling vessels, as compared with the conventional sampling vessels, the time required for analysis can be greatly shortened, and the gradient of the cooling curve in eutectic can be reduced. Thus, a sampling vessel with high performance can be obtained. The dimensions of the sample chamber are reduced as compared with those of the conventional sample chamber. In the probe-type sampling vessel in the invention, therefore, the pushing force required for immersing the vessel into the melt can be reduced.

According to the probe-type sampling vessel in the invention of claim 3, the members which are separated from each other in the dividing plane that does not cross the sample chamber are bonded in the dividing plane. Thus, there is no fear that the adhesive agent for bonding is contaminated with the melt in the sample chamber. In addition, the bonding area is reduced as compared with the conventional structure which is divided into right and left members, so that the bonding operation is easily performed. Moreover, warping hardly occurs during a process of firing each member, so that the production and inspection steps can be remarkably simplified as compared with the conventional probe-type sampling vessel.

According to the probe-type sampling vessel in the invention of claim 4, the configuration in which the runner and the exhaust passage communicate with each other on a straight line is adopted. With this configuration, the internal structure of the vessel is simplified, and the melt smoothly flows into the sample chamber via the runner. Thus, there is no fear that disadvantages such as that the melt is solidified in the runner occur.

What is claimed is:

1. A sampling vessel for thermal analysis of molten metal comprising:

a cylindrical bottomed sample chamber having an opening in an upper end and a bottom wall;

a runner formed adjacent to said sample chamber having an opened lower end communicating with said opening of said sample chamber;

an exhaust passage communicating with said opening of said sample chamber having an opened upper end in a position higher than said opening of said sample chamber;

a sensor holder formed above said sample chamber;

a temperature sensor inserted into said sample chamber through said opening of said sample chamber;

said temperature sensor being held by said sensor holder;

said sample chamber having a diameter in a range of 16 to 24 mm and a depth of at least 36 mm;

said temperature being sensor positioned away from the bottom wall of said sample chamber by 7 to 22 mm; and said vessel being configured by having shapes which are formed by dividing said vessel by a dividing plane that perpendicularly crosses a center axis of said vessel in a position which is above said sample chamber and not in said sample chamber, and said members being bonded together at the dividing plane.

2. A sampling vessel for thermal analysis of molten metal according to claim 1, wherein said runner and said exhaust passage communicate with each other on a straight line.

3. A sampling vessel for thermal analysis of molten metal according to claim 1, wherein a circumference wall of said sample chamber has a thickness of 5.5 mm or more.

* * * * *